United States Patent
Cross et al.

(10) Patent No.: US 8,084,229 B2
(45) Date of Patent: Dec. 27, 2011

(54) GDEP ENHANCER ELEMENT AND USE THEREOF TO CONFER RETINAL SPECIFIC GENE EXPRESSION

(75) Inventors: Deanna S. Cross, Wausau, WI (US); James K. Burmester, Marshfield, WI (US)

(73) Assignee: Marshfield Clinic, Marshfield, WI (US)

( * ) Notice: Subject to any disclaimer, the term of this patent is extended or adjusted under 35 U.S.C. 154(b) by 0 days.

(21) Appl. No.: 12/344,762

(22) Filed: Dec. 29, 2008

(65) Prior Publication Data

US 2009/0170161 A1    Jul. 2, 2009

Related U.S. Application Data

(60) Provisional application No. 61/017,284, filed on Dec. 28, 2007.

(51) Int. Cl.
| | |
|---|---|
| *C12P 21/00* | (2006.01) |
| *C07H 21/02* | (2006.01) |
| *C12N 7/01* | (2006.01) |
| *C12N 15/63* | (2006.01) |
| *C12N 5/10* | (2006.01) |

(52) U.S. Cl. ............... 435/69.1; 536/23.5; 536/24.1; 435/235.1; 435/320.1; 435/325

(58) Field of Classification Search ............. 435/69.1, 435/235.1, 320.1, 325; 536/24.1, 23.5
See application file for complete search history.

(56) References Cited

OTHER PUBLICATIONS

NCBI accession No. AC118141, dated Oct. 15, 2002.*
Ecke et al., Goodman & Gilman's The Pharmacological basis of Therapeutics, McGraw-Hill, New York, NY. 1996, pp. 77-101.*
Thomas et al. Nature Rev.Genet. 4: 346-358; 2003.*
Verma et al Annu Rev Biochem. 2005;74:711-38.*
Pleyer et al. Progress in Retinal and Eye Research 22 (2003) 277-293.*
Kamata et al. Mol Ther. 2001, 4(4): 307-312.*
Frengen et al Genomics, 1999, 58, 250-253.*
Ralph et al Clinical Science, 2006, 110, 37-46.*
Acland et al Mol. Ther., 2005, 12(6), 1072-1082.*
Cross et al Med. Oncol., 2008, 25, 40-49.*
Cross DS, et al. Functional characterization of the GDEP promoter and three enhancer elements in retinoblastoma and prostate cell lines. Med Oncol. 2008;25:40-49. Epub Jun. 27, 2007.

* cited by examiner

*Primary Examiner* — Anoop Singh
(74) *Attorney, Agent, or Firm* — Quarles & Brady, LLP

(57) ABSTRACT

The present invention is directed to isolated nucleic acids containing functional polynucleotide sequences representing an enhancer element for the Gene Differentially Expressed in Prostate (GDEP). Such molecules are useful in conferring retinal specific transcriptional responsiveness on associated promoters and methods for directing retinal specific gene expression are accordingly disclosed.

11 Claims, 7 Drawing Sheets

SEQUENCE LISTING

<160> NUMBER OF SEQ ID NOS: 28

<210> SEQ ID NO 1
<211> LENGTH: 660
<212> TYPE: DNA
<213> ORGANISM: Human

<400> SEQUENCE: 1

```
aggccctgag cacaattaca aaccaaacca gattcatcca ctgaagcctc ttcccttttg    60
acgtttcaa  tcatcatctt ttccttttct attagatttt gaatatcctt aagtggcact   120
catctgatgt taaagtgtca cgccttgtgc catgcctcag cctgatgttc ctcatgacag   180
tgttctaaat cttatcccaa ccaaaattca cttgtgcatt gccccttcct ccttgttcta   240
tcatcacaaa atctgtggta tttaattggt atgtagtttc aataagaact gatgagctga   300
ctaggttcaa atgttgggaa ggccatctag aaattatcga ttatgccaaa aagcaaagct   360
aagagagaga cttccaagcc atacttgata ctggagaaga ctgtatttgc aactatttca   420
agtttctgct attccttggc catcaatgcc ttcttcacat tgtggttatg tcattatata   480
ttttcactcc tgtaggagaa gacttaaaac attttttta  aattcttaag ttattgtctc   540
tttattgcac tgcaattttg tctgttgctt agaatttgtg atggaaagaa attcccagca   600
ccttgtaatc caggtcttag cctttccagt ctatccagat tgctcagtta aaccccagct   660
```

<210> SEQ ID NO 2
<211> LENGTH: 28
<212> TYPE: DNA
<213> ORGANISM: Artificial Sequence
<220> FEATURE:
<223> OTHER INFORMATION: PCR Primer

<400> SEQUENCE: 2
cgggatcctc ttctgcctcc ctctctca    28

<210> SEQ ID NO 3
<211> LENGTH: 30
<212> TYPE: DNA
<213> ORGANISM: Artificial Sequence
<220> FEATURE:
<223> OTHER INFORMATION: PCR Primer

<400> SEQUENCE: 3
ggggtacctt ttcaaggtgc tcagttttca    30

<210> SEQ ID NO 4
<211> LENGTH: 30
<212> TYPE: DNA
<213> ORGANISM: Artificial Sequence
<220> FEATURE:
<223> OTHER INFORMATION: PCR Primer

<400> SEQUENCE: 4

-continued ggggtaccca ttttaaggga aagaatgagc                                                30

<210> SEQ ID NO 5
<211> LENGTH: 25
<212> TYPE: DNA
<213> ORGANISM: Artificial Sequence
<220> FEATURE:
<223> OTHER INFORMATION: PCR Primer

<400> SEQUENCE: 5
ggggtaccag ttatgtccaa tgata                                                     25

<210> SEQ ID NO 6
<211> LENGTH: 26
<212> TYPE: DNA
<213> ORGANISM: Artificial Sequence
<220> FEATURE:
<223> OTHER INFORMATION: PCR Primer

<400> SEQUENCE: 6
ggggtaccac tacccgatct ccaacc                                                    26

<210> SEQ ID NO 7
<211> LENGTH: 26
<212> TYPE: DNA
<213> ORGANISM: Artificial Sequence
<220> FEATURE:
<223> OTHER INFORMATION: PCR Primer

<400> SEQUENCE: 7
ggggtaccta ataccattcc ggcagt                                                    26

<210> SEQ ID NO 8
<211> LENGTH: 26
<212> TYPE: DNA
<213> ORGANISM: Artificial Sequence
<220> FEATURE:
<223> OTHER INFORMATION: PCR Primer

<400> SEQUENCE: 8
ggggtaccaa ggaggcttaa cacagc                                                    26

<210> SEQ ID NO 9
<211> LENGTH: 30
<212> TYPE: DNA
<213> ORGANISM: Artificial Sequence
<220> FEATURE:
<223> OTHER INFORMATION: PCR Primer

<400> SEQUENCE: 9
acgcgtcgac gcttcctgct gtggctaatc                                                30

<210> SEQ ID NO 10
<211> LENGTH: 29
<212> TYPE: DNA
<213> ORGANISM: Artificial Sequence
<220> FEATURE:
<223> OTHER INFORMATION: PCR Primer

<400> SEQUENCE: 10
acgcgtcgac caaaggccgt actgatgtt                                                 29

<210> SEQ ID NO 11
<211> LENGTH: 34
<212> TYPE: DNA
<213> ORGANISM: Artificial Sequence
<220> FEATURE:

<223> OTHER INFORMATION: PCR Primer

<400> SEQUENCE: 11
acgcgtcgac agctagtaga gagtctattg gaca    34

<210> SEQ ID NO 12
<211> LENGTH: 34
<212> TYPE: DNA
<213> ORGANISM: Artificial Sequence
<220> FEATURE:
<223> OTHER INFORMATION: PCR Primer

<400> SEQUENCE: 12
acgcgtcgac tcatgtaatc aataaccatc tgtt    34

<210> SEQ ID NO 13
<211> LENGTH: 34
<212> TYPE: DNA
<213> ORGANISM: Artificial Sequence
<220> FEATURE:
<223> OTHER INFORMATION: PCR Primer

<400> SEQUENCE: 13
acgcgtcgac caaacaactg tgtgaagtga attc    34

<210> SEQ ID NO 14
<211> LENGTH: 34
<212> TYPE: DNA
<213> ORGANISM: Artificial Sequence
<220> FEATURE:
<223> OTHER INFORMATION: PCR Primer

<400> SEQUENCE: 14
acgcgtcgac aagtatgtgc taataaacaa agat    34

<210> SEQ ID NO 15
<211> LENGTH: 30
<212> TYPE: DNA
<213> ORGANISM: Artificial Sequence
<220> FEATURE:
<223> OTHER INFORMATION: PCR Primer

<400> SEQUENCE: 15
acgcgtcgac gcttcctgct gtggctaatc    30

<210> SEQ ID NO 16
<211> LENGTH: 30
<212> TYPE: DNA
<213> ORGANISM: Artificial Sequence
<220> FEATURE:
<223> OTHER INFORMATION: PCR Primer

<400> SEQUENCE: 16
acgcgtcgac accaatcttt ctggtccatc    30

<210> SEQ ID NO 17
<211> LENGTH: 36
<212> TYPE: DNA
<213> ORGANISM: Artificial Sequence
<220> FEATURE:
<223> OTHER INFORMATION: PCR Primer

<400> SEQUENCE: 17
acgcgtcgac gataaaactg taaactgtga gcagaa    36

<210> SEQ ID NO 18

<211> LENGTH: 29
<212> TYPE: DNA
<213> ORGANISM: Artificial Sequence
<220> FEATURE:
<223> OTHER INFORMATION: PCR Primer

<400> SEQUENCE: 18
acgcgtcgac agggcttgcc tgaatagac                              29

<210> SEQ ID NO 19
<211> LENGTH: 33
<212> TYPE: DNA
<213> ORGANISM: Artificial Sequence
<220> FEATURE:
<223> OTHER INFORMATION: PCR Primer

<400> SEQUENCE: 19
acgcgtcgac tcctgagaca attgtgcata aaa                         33

<210> SEQ ID NO 20
<211> LENGTH: 34
<212> TYPE: DNA
<213> ORGANISM: Artificial Sequence
<220> FEATURE:
<223> OTHER INFORMATION: PCR Primer

<400> SEQUENCE: 20
acgcgtcgac tgtacacctg cttcaagtct tttc                        34

<210> SEQ ID NO 21
<211> LENGTH: 30
<212> TYPE: DNA
<213> ORGANISM: Artificial Sequence
<220> FEATURE:
<223> OTHER INFORMATION: PCR Primer

<400> SEQUENCE: 21
acgcgtcgac aagtggttaa atgtccaaaa                             30

<210> SEQ ID NO 22
<211> LENGTH: 30
<212> TYPE: DNA
<213> ORGANISM: Artificial Sequence
<220> FEATURE:
<223> OTHER INFORMATION: PCR Primer

<400> SEQUENCE: 22
acgcgtcgac atcaacaagg gacccattca                             30

<210> SEQ ID NO 23
<211> LENGTH: 35
<212> TYPE: DNA
<213> ORGANISM: Artificial Sequence
<220> FEATURE:
<223> OTHER INFORMATION: PCR Primer

<400> SEQUENCE: 23
acgcgtcgac aaacaactgt gtgaagtaga ttctg                       35

<210> SEQ ID NO 24
<211> LENGTH: 30
<212> TYPE: DNA

```
<213> ORGANISM: Artificial Sequence
<220> FEATURE:
<223> OTHER INFORMATION: PCR Primer

<400> SEQUENCE: 24
acgcgtcgac tcaaaaggga agaggcttca                              30

<210> SEQ ID NO 25
<211> LENGTH: 30
<212> TYPE: DNA
<213> ORGANISM: Artificial Sequence
<220> FEATURE:
<223> OTHER INFORMATION: PCR Primer

<400> SEQUENCE: 25
acgcgtcgac aggccctgag cacaattaca                              30

<210> SEQ ID NO 26
<211> LENGTH: 30
<212> TYPE: DNA
<213> ORGANISM: Artificial Sequence
<220> FEATURE:
<223> OTHER INFORMATION: PCR Primer

<400> SEQUENCE: 26
acgcgtcgac agctggggtt taactgagca                              30

<210> SEQ ID NO 27
<211> LENGTH: 30
<212> TYPE: DNA
<213> ORGANISM: Artificial Sequence
<220> FEATURE:
<223> OTHER INFORMATION: PCR Primer

<400> SEQUENCE: 27
acgcgtcgac tggaaagaaa ttcccagcac                              30

<210> SEQ ID NO 28
<211> LENGTH: 30
<212> TYPE: DNA
<213> ORGANISM: Artificial Sequence
<220> FEATURE:
<223> OTHER INFORMATION: PCR Primer

<400> SEQUENCE: 28
acgcgtcgac tttttcccct gggctaagat                              30
```

GDEP ENHANCER ELEMENT AND USE THEREOF TO CONFER RETINAL SPECIFIC GENE EXPRESSION

CROSS-REFERENCE TO RELATED APPLICATION

This non-provisional application claims the benefit of U.S. Provisional application 61/017284, filed Dec. 28, 2007, which is incorporated herein by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to methods for providing tissue specific expression of a transgene. More particularly, the present invention relates to the use of a enhancer element of the Gene Differentially Expressed in Prostate (GDEP) to confer retinal specific expression of a transgene.

BACKGROUND OF THE INVENTION

While modern medicine has been successful in treating numerous human conditions, a large number still remain outside the scope of effective treatment. Gene therapy is one method of potentially treating diseases that are currently untreatable. However, successful gene therapy requires improvements in delivery of the target gene (1). To increase the safety and efficacy of gene therapy agents, tissue specific promoter elements are being incorporated into the delivery vectors (2). This is particularly true for gene therapy agents developed to treat cancers that originate from a particular tissue or cell lineage (3). While tissue specific promoters restrict expression of the gene therapy agent to target tissues, they often direct only low levels of gene expression within the targeted cells (2). To increase gene expression to therapeutic levels a number of enhancer elements have been used (2). However, only a limited number of tissue specific promoter and enhancer elements have been described thus far, making it important to continue to identify additional tissue specific regulatory sequences that may be developed for gene therapy.

GDEP (gene differentially expressed in prostate cancer, aka., PCAN1), a newly discovered gene with remarkable tissue specificity, is a promising candidate for regulatory analysis because it exhibits a high level of expression that is limited to two tissues, the retina and the prostate (4,5,6). As these two tissues have different origins and disparate functions it is likely that the regulatory mechanisms responsible for expression are not shared in their entirety. In addition, both the retina and prostate are prime targets for gene therapy (7,8).

GDEP expression in prostate tissue has been previously documented. GDEP was initially identified through dbEST data mining for prostate specific genes (4). The high level of prostate specific expression was confirmed using Northern Blot analysis and reverse transcriptase PCR (4,5,6). GDEP is expressed exclusively in the prostate epithelial cells, particularly basal epithelial cells, and not in the surrounding stromal prostate tissue (4,5). GDEP is also expressed in a number of prostate cell lines and this expression is enhanced when cells are grown in the presence of Matrigel suggesting that paracrine factors influence GDEP expression (6). Furthermore, GDEP expression is insensitive to testosterone treatment (5,6) making this gene a potential vehicle for investigating prostate specific but testosterone independent regulation.

In addition to prostate expression, GDEP is highly expressed in neural retinal tissue as well as retinoblastoma cell lines (6). Neural retinal tissue from both male and female donors was tested for GDEP expression to ensure that expression was not sex limited. All tissue exhibited a high level of GDEP transcript when compared to actin using RT-PCR. Retinoblastoma cell lines Y79 and WERI-Rb-1 were also both positive for GDEP expression. In contrast, ARPE-19 (a retinal pigmented epithelial cell line) exhibited no expression of this gene, making this gene specific to the cell types found in the neural retina and not the surrounding retinal tissue (6).

As can be appreciated, GDEP is a promising candidate for regulatory analysis because it exhibits a high level of expression that is limited to two tissues, the retina and the prostate. To date there have been no functional studies of the GDEP promoter. Therefore, gaining an understanding of how GDEP is regulated in the tissue specific context and identifying the sequences responsible for this regulation are important goals. Identification of such sequences would open routes for a wide variety of practical applications including, but not limited to, novel methods for tissue specific gene therapy.

SUMMARY OF THE INVENTION

The present invention is based on the inventors' efforts to characterize functional regulatory regions related to GDEP. The inventors identified an enhancer element located in the 40 KB intron of GDEP and demonstrated the enhancer element capable of increasing reporter gene expression in a retinoblastoma cell line approximately eight fold. Accordingly, the respective polynucleotide sequence is a strong retinal specific enhancer. That respective GDEP enhancer element is the polynucleotide sequence set forth in SEQ ID NO:1 and isolated nucleic acids, vectors, host cells and methods of using the enhancer for retinal specific gene expression are described and claimed herein.

In a first aspect, the present invention provides an isolated nucleic acid comprising the human GDEP enhancer sequence set forth in SEQ ID NO:1 or a sequence with substantial sequence homology thereto and capable of conferring retinal specific responsiveness on an operably linked gene promoter. Certain isolated nucleic acids further include a gene promoter that is operably linked to the enhancer sequence. The gene promoter is preferably a heterologous gene promoter such as, for example, the SV40 promoter.

Certain isolated nucleic acids also include a gene linked to the promoter to be expressed in a retinal specific manner via the GDEP enhancer element. The gene is preferably a heterologous gene. The isolated nucleic acid including the enhancer element and promoter, optionally with or without the gene to be expressed, may be in the form of an expression vector.

In certain embodiments, the invention provides a vector for treating retinal-related conditions by gene therapy. Such vectors include: (a) a therapeutic gene under control of a gene promoter; and (b) the human GDEP enhancer sequence set forth in SEQ ID NO:1 or a sequence with substantial sequence homology thereto. The sequence is operably linked to the gene promoter and confers retinal specific expression on the therapeutic gene. Such vectors preferably utilize a heterologous promoter and take the form of a virus vector such as, for example, an adeno-virus vector, an adeno-associated virus (AAV) vector, or a retrovirus.

Yet another aspect of the invention encompasses host cells that have been transformed with the isolated GDEP enhancer element, most preferably in the form of an expression vector which includes a heterologous gene of interest to be expressed in a retinal specific manner. Accordingly, preferred host cells include primary cultured neural retinal cells and immortalized retinal cells that provide a suitable retinal specific background in which the GDEP enhancer element functions in a tissue specific manner.

The invention also provides methods for retinal specific expression of a gene. Such methods include steps of: (a) providing a host cell containing: (i) a heterologous gene promoter; (ii) a gene operably linked to the heterologous gene promoter; and (iii) the enhancer sequence set forth in SEQ ID NO:1 or a sequence with substantial sequence homology thereto wherein the enhancer sequence is operably linked to the gene promoter and confers retinal specific responsiveness thereon; and (b) subjecting the host cell to conditions suitable for retinal specific expression of the gene. The gene to be expressed in such methods is preferably a heterologous gene.

The invention further encompasses methods for treating a retinal-related condition by gene therapy. Such a method includes the step of administering to an individual in need of such gene therapy an inventive vector described herein. Certain methods provide for retinal specific expression of a therapeutic gene and include the step of administering to an individual in need of retinal specific expression of a therapeutic gene a vector according to the invention.

In another aspect of the invention, methods of screening for an agent that may alter the activity of an enhancer sequence for GDEP gene are provided. Such methods include steps of: (a) providing a nucleic acid comprising (i) a gene promoter; (ii) a reporter gene operably linked to the gene promoter; and (iii) the enhancer sequence for GDEP as set forth in SEQ ID NO:1 wherein the enhancer sequence is operably linked to the gene promoter to confer retinal specific responsiveness thereon; (b) subjecting the nucleic acid to conditions suitable for the enhancer sequence to enhance expression of the reporter gene in the presence of the test agent; and (c) evaluating the expression of the reporter gene compared to a control nucleic acid that is exposed to the same conditions but without the test agent wherein a higher or lower expression than that of the control nucleic acid indicates that the agent may alter GDEP enhancer sequence activity.

As can be appreciated, it is one object of the present invention to provide methods for conferring transcriptional responsiveness on heterologous promoters operably linked to the GDEP enhancer element described and claimed herein. This invention provides the advantage over prior technologies in that embodiments of the invention utilize or are based on a highly retinal specific enhancer element, as recently discovered and characterized by the present inventors. Other objects, features and advantages of the present invention will become apparent after review of the specification, claims and drawings.

DETAILED DESCRIPTION OF THE INVENTION

I. In General

Figure 1:
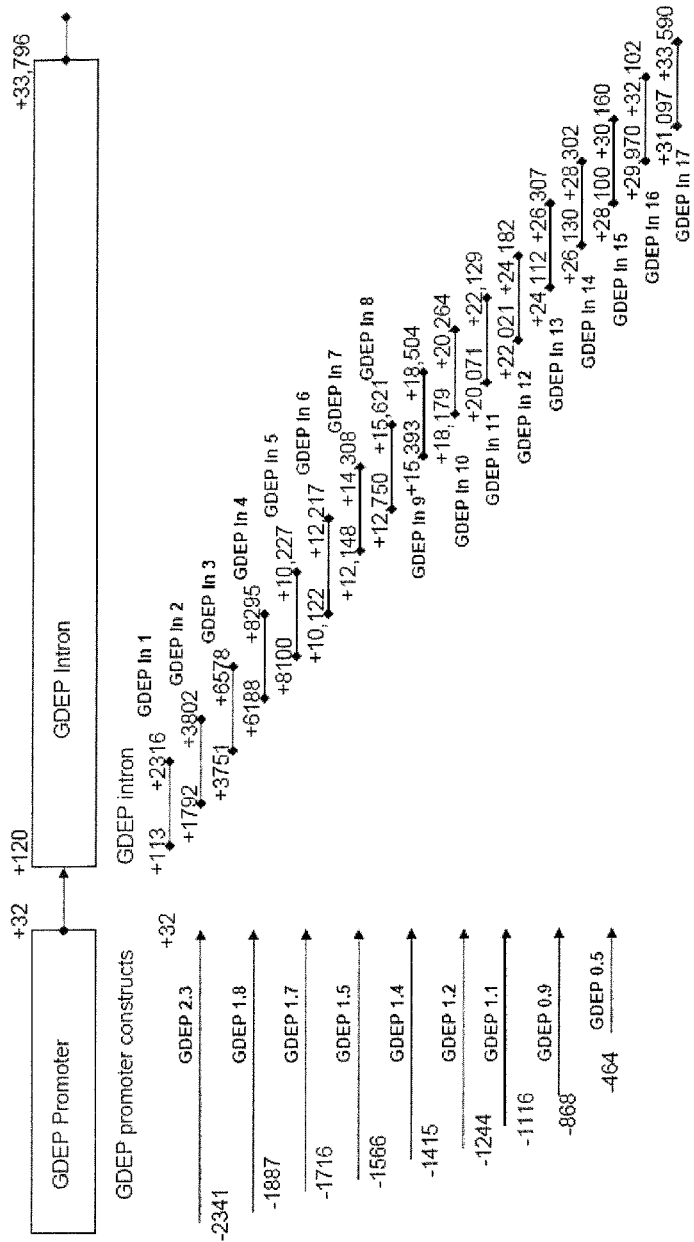
FIG. 1 provides a schematic of promoter and enhancer deletion constructs created for GDEP expression vectors.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The terms "enhancer", "enhancer element", or "enhancer sequence" refer to a DNA segment comprising one or more similar or different response elements capable of being operably linked to a promoter to confer, via binding or otherwise interacting with a receptor or other transcription factor or a combination of dissimilar factors, responsiveness to transcriptional activity of the promoter.

The "GDEP enhancer" (also termed "GDEP enhancer element" or "GDEP enhance element sequence") described and claimed herein refers to the polynucleotide sequence of SEQ ID NO:1 as set forth in its entirety in the following Examples section. As described herein, the respective polynucleotide sequence was isolated by the present inventors from Intron 13 of human GDEP and is capable of conferring retinal specific expression on an operably linked heterologous promoter/gene construct.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

A "host cell" is a cell which has been transformed or transfected, or is capable of transformation or transfection by an exogenous polynucleotide sequence. Preferred host cells for use in methods of the invention include primary and immortalized neural retinal cell lines such as, for example, the retinoblastoma cell line Y79 which, when transformed with an expression vector containing the GDEP enhancer element, provide conditions suitable for driving retinal cell specific expression of the expression vector via the GDEP enhancer element.

The term "substantial sequence homology" refers to DNA or RNA sequences which have de minimus sequence variations from, and retain substantially the same biological functions as the corresponding sequences to which comparison is made. In the present invention, it is intended that sequences having substantial sequence homology to the GDEP enhancer element of the SEQ ID NO: 1 are identified by: (1) their ability to direct retinal specific activation of non-GDEP promoters in a manner substantially identical to the GDEP enhancer element of SEQ ID NO: 1; and (2) their ability to hybridize to the sequence of SEQ ID NO: 1 under stringent conditions. A sequence's ability to direct retinal specific activation of non-GDEP promoters may be assayed in a manner substantially similar to that disclosed in the present examples section; sequences to be assayed are cloned into expression vectors containing a heterologous promoter and reporter gene and the recombinant construct is subsequently assayed for retinal specific activation relative to control constructs driven by the presently-claimed GDEP enhancer element of SEQ ID NO:1.

As used herein, "hybridizes under stringent conditions" is intended to describe conditions for hybridization and washing under which nucleotide sequences that are significantly identical or homologous to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chlorine/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 4×SSC plus 50% formamide at about 42-50° C.) followed by one or more washes in 0.3×SSC, at about 65-70° C. A preferred, non-limiting example of highly stringent hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM NaH$_2$PO$_4$, and 1.25 mM EDTA, pH 7.4) can be substituted for SSC (1×SSPE is 0.15 M NaC and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature (T$_m$) of the hybrid, where T$_m$ is determined according to the following equations. For hybrids less than 18 base pairs in length, T$_m$ (° C.)=2(# of A+T bases)+4(# of G+C bases). For hybrids between 18 and 49 base pairs in length, T$_m$ (° C.)=81.5+16.6(log$_{10}$[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional preferred, non-limiting example of stringent hybridization conditions is hybridization in 0.25-0.5M NaH$_2$PO$_4$, 7% SDS at about 65° C., followed by one ore more washed at 0.02M NaH$_2$PO$_4$, 1% SDS at 65° C., see e.g., Church and Gilbert (1984) Proc. Natl. Acad. Sci. USA 81: 1991-1995, (or alternatively 0.2×SSC, 1% SDS).

"Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

The term "operably linked" means that the linkage (e.g., DNA segment) between the DNA segments so linked is such that the described effect of one of the linked segments on the other is capable of occurring. "Linked" shall refer to physically adjoined segments and, more broadly, to segments which are spatially contained relative to each other such that the described effect is capable of occurring (e.g., DNA segments may be present on two separate plasmids but contained within a cell such that the described effect is nonetheless achieved). Effecting operable linkages for the various purposes stated herein is well within the skill of those of ordinary skill in the art, particularly with the teaching of the instant specification.

The term "reporter gene" refers to any gene of interest where the transcription of the gene, translation of the gene product, and/or activity of the gene product can be measured. Polymerase chain reaction (PCR) may be used to measure the transcription of the reporter gene. Additionally, a detectably labeled probe specific to the reporter gene could be used to quantify the amount of reporter gene transcribed. Translation of the reporter gene may be done through use of an ELISA using an antibody specific to the reporter gene and a secondary antibody that recognizes the initial antibody. If the reporter gene is an enzyme, the activity of the enzyme may be measured using detectable substrates for the enzyme activity.

As used herein the term "gene product" shall refer to the biochemical material, either RNA or protein, resulting from expression of a gene.

The term "heterologous" is used for any combination of DNA sequences that is not normally found intimately associated in nature (e.g., a reporter gene operably linked to a SV40 promoter; a GDEP enhancer element operably linked to a SV40 promoter). As well, a "heterologous gene" shall refer to a gene not naturally present in a host cell (e.g., a luciferase gene present in a cell of retinoblastoma cell line Y79).

The nucleotides which occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

II. The Invention

Regulatory regions capable of driving DNA expression in a particular tissue are of increasing interest because of the potential for these elements to be incorporated into gene therapy. Tissue specific regulatory agents are increasingly being used in such therapeutics to increase safety by ensuring that the target gene is active only in the desired tissues.

The present invention is based on the inventors' investigations of the regions of DNA that are responsible for tissue specific expression of GDEP in prostate and retinal cells. The inventors have isolated a 1.5 KB prostate specific promoter from the proximal region of GDEP. A smaller 0.5 KB promoter exhibited minimal activity in the retinoblastoma cell line Y79 but not in the prostate cells tested. In addition, the inventors investigated three enhancer elements located in the 40 KB intron of GDEP. They identified two enhancer elements that increase reporter gene expression in prostate cell line LnCAP by approximately two fold over the SV40 enhancer and one enhancer element that increases expression in the Y79 cell line approximately eight fold making it a strong retinal specific enhancer.

Like most tissue specific promoters, the GDEP promoter exhibited a consistent but low level of reporter gene expression. The inventors determined that prostate specific expression from the 1.5 KB promoter fragment was 3.6 times greater than the promoterless control vector. This level of expression is similar to the low level of reporter gene expression seen with the DD3 promoter in the LnCAP cell line (10). Both of these genes exhibit much lower expression in the LnCAP cell line than in prostate tissue and this lack of expression may be due to paracrine factors found in tissue and not in cell culture (6, 10). Expression of GDEP is increased in the presence of Matrigel (6).

Tissue specific promoters that are currently being used as gene therapy agents exhibit low basal levels of reporter gene induction. For instance, the basal 600 base pair PSA promoter and the highly related KLK2 promoter exhibit very low levels of reporter gene expression in the presence and absence of testosterone, 0.1-0.3% of the control vector (11, 12). The basal PSMA promoter is also incapable of inducing high levels of gene expression in LnCAP with basal promoter expression only about 2 fold that of a promoterless control (13).

Two factors make the GDEP promoter unique from other prostate tissue promoters. Unlike other prostate specific promoters, the 1.5 KB GDEP promoter does not induce expression in non prostate cell lines. The promoter was tested in MCF 7 breast cancer cell lines as well as retinoblastoma cell line Y79 where GDEP is expressed and neither of these exhibited reporter gene expression. This contrasts with the basal promoter of PSA and PSMA that are expressed in a number of cell lines (14, 15). In one instance the PSA promoter was used in vivo in a mouse model for gene therapy the gene therapy agent accumulated in the lungs and not the prostate (16). Secondly, the GDEP promoter was androgen insensitive (data not shown). This contrasts with the PSA promoter which is induced with androgens (17). One other androgen insensitive prostate specific promoter has been described, that of the PSGR gene. The dual PSGR promoters are in fact highly activated by IL-6 but not androgen (18).

Increases in tissue specific expression have been obtained using tissue specific enhancers. The inventors identified two regions of the 40 KB intron of the gene encoding GDEP that markedly increased promoter activity in prostate cells. These elements both increased expression of the SV40 promoter approximately two fold greater the SV40 control vector, a widely used vector that drives strong constitutive expression in many cellular types.

To date the prostate specific enhancers identified and used in gene therapy are androgen responsive. The PSA enhancer is a region 4.2 KB upstream of the proximal PSA promoter that contains a strong functional androgen response element that increases the specificity and activity of a homologous or heterologous promoter when exposed to androgen (19, 20). The PSMA enhancer region in the $3^{rd}$ intron is sharply down regulated by androgens. When used in combination with the PSMA promoter, high levels of gene expression are achieved in the absence of testosterone while low to moderate expression occurs in the presence of testosterone (21). These enhancer elements have been used in a number of heterologous promoter systems in an attempt to maximize both prostate specificity and activity (22). One strategy has been to balance the androgen sensitivities of these two enhancer regions by using them in combination (23, 24). In the present experiments, the GDEP enhancer elements were placed 3' of the gene while the PSMA and PSA enhancers have been cloned directly in front of the promoter regions.

The inventors further identified regulatory regions that are capable of driving retinal cell expression. The 0.5 KB GDEP promoter exhibited a very low level of basal expression in the Y79 cell line with expression only 1.6 times greater than the no promoter basic control vector. This contrasts with the high level of GDEP expression observed in the Y79 cell line. It was likely that essential elements to increase expression in the retina lie outside the proximal 2.4 KB region tested. Enhancer elements have been found with other retina specific genes. For instance the interphotoreceptor retinoid-binding protein (IRBP) has a minimal promoter of 274-350 base pairs, however tissue specific expression is increased when a 209-220 base pair enhancer located approximately 1.5 KB upstream of the transcription initiation start site is incorporated into reporter vectors (25, 26). Highly conserved enhancer regions identified in *Drosophila* also lie both proximal and distal to the dachshund gene promoter (27). One enhancer of the dachshund gene is conserved across many species (28).

The GDEP enhancer that the inventors subsequently identified in the GDEP intron increased expression approximately eight times over that of the control vector with the SV40 enhancer. This increase in expression is of at least the same magnitude as other described retinal specific enhancers. One of the advantages the GDEP promoter provides over other described retinal enhancers is that it increases expression with a heterologous promoter, SV40. In contrast the mouse rhodopsin enhancer region is highly cell type specific increasing expression in only the rod photoreceptor cells and exhibits promoter specificity failing to increase reporter gene expression when combined with the heterologous hsp70 A1 promoter (29). The Pax 6 enhancer from quail located in the $4^{th}$ intron of the gene was placed 3' of a number of homologous and heterologous promoters and activity was variable depending on the promoter it was paired with, failing to enhance expression from one of the known Pax-QNR promoters (30). It is conceivable and within the present invention to operably link the GDEP enhancer region with several known neural retinal specific promoters such as the rhodopsin promoter (a photoreceptor specific promoter) and the Platelet-derived growth factor, PDGF, promoter (a retinal ganglion specific promoter) to affect an increase in activity of these tissue specific promoters.

Accordingly, the present invention provides an isolated nucleic acid including a polynucleotide sequence from a GDEP intron region that is capable of conferring transcriptional responsiveness on an operably linked heterologous promoter. The invention further encompasses isolated nucleic acids having substantial sequence homology and substantially identified retinal tissue specific function to the GDEP enhancer element set forth in SEQ ID NO: 1. Accordingly, the claimed nucleic acids shall not be limited to the specific examples set forth herein; the present invention encompasses gene upstream sequences which have de minimus sequence variations from, and retain substantially identical retinal tissue specific enhancer function relative to the human GDEP enhancer sequence disclosed and claimed herein.

A nucleic acid molecule of the present invention, e.g., a nucleic acid molecule having the nucleotide sequence of SEQ ID NO: 1 can be isolated using standard molecular biology techniques and the sequence information provided herein. Using all or portion of the nucleic acid sequence of SEQ ID NO: 1 as a hybridization probe nucleic acid molecules can be isolated using standard hybridization and cloning techniques (e.g., as described in Sambrook, J., Fritsh, E. F., and Maniatis, T. Molecular Cloning: A Laboratory Manual, 2.sup.nd. ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1 can be isolated by the polymerase chain reaction (PCR) using synthetic oligonucleotide primers designed based upon the sequence of SEQ ID NO: 1. A nucleic acid according to the invention can be amplified using cDNA, mRNA or, alternatively, genomic DNA as a template and appropriate oligonucleotide primers according to standard PCR amplification techniques. For example, the primers identified as SEQ ID NOs: 25 and 26 may be used to amplify the presently claimed enhancer element from human genomic DNA. Furthermore, oligonucleotides corresponding to the GDEP enhancer nucleotide sequences can be prepared by standard synthetic techniques, e.g., using an automated DNA synthesizer.

In a preferred embodiment, the isolated nucleic acid molecules of the invention comprise the nucleotide sequence shown in SEQ ID NO: 1, a complement of the nucleotide sequence shown in SEQ ID NO: 1, or a portion of any of these nucleotide sequences which retains the ability to confer retinal specific expression on an operably linked heterologous promoter/gene. A nucleic acid molecule which is complementary to the nucleotide sequence shown in SEQ ID NO: 1, is one which is sufficiently complementary to the nucleotide sequence shown in SEQ ID NO: 1 such that it can hybridize under stringent conditions to the nucleotide sequence shown in SEQ ID NO: 1 thereby forming a stable duplex.

In still another preferred embodiment, an isolated nucleic acid molecule of the present invention comprises a nucleotide sequence which is at least about 80%, 85%, 90%, 91%, 92%, 93%, 94%, 95%, 96%, 97%, 98%, 99% or more identical to the entire length of the nucleotide sequence shown in SEQ ID NO: 1. Yet other embodiments consist wholly of an isolated nucleic acid with a nucleotide sequence which is at least 80%, 85%, 90%, 91%, 92%, 93%, 94%, 95%, 96%, 97%, 98%, 99% or more identical to the entire length of the nucleotide sequence of SEQ ID NO: 1. Such sequences have the ability to confer retinal specific expression when cloned into an operably linked position relative to a heterologous promoter/gene.

To determine the percent identity of two nucleic acids, the sequences are aligned for optimal comparison purposes. The percent identity between the two sequences is a function of the number of identical positions shared by the sequences (i.e., percent identity is equal to the number of identical positions/total number of positions (e.g., overlapping positions) multiplied by 100). The sequences to be compared may of the same length or, alternatively, of differing lengths. The percent identity between two sequences can be determined with or without allowing gaps. In calculating percent identity, typically only exact matches are counted. The determination of percent identity between two sequences can be accomplished using one of several mathematical algorithms commonly known and available to those of skill in the art.

In certain isolated nucleic acids, a promoter is included in the molecule that is subject to transcriptional activation by the GDEP enhancer sequence. With respect to the promoter which is acted upon by the GDEP enhancer element, practically any promoter may be used, so long as the transcriptional activity of such a promoter can be modulated by the enhancer element of the present invention (when suitably provided or positioned in operable fashion relative to the promoter). The promoter may be the native GDEP promoter, in an isolated minimal form, or, alternatively, a promoter not naturally under control of GDEP enhancer elements (i.e., a heterologous promoter). Preferred heterologous promoters for use in the invention include, but not limited to, the SV40 promoter. Other exemplary promoters for use in combination with the enhancer element include the rhodopsin kinase (GRK1) promoter, the guanylate cyclase activator1A, (GUCA1A) promoter, and the Yin Yang 1(YY1), interphotoreceptor binding protein (IRBP) promoter. As those of ordinary skill in the art will understand, the enhancer element of the present invention, like other enhancer elements, are orientation and, with wide latitude, position independent. Thus, the enhancer element of the present invention is functional in either orientation and may be placed in any convenient location from the promoter to be affected. Positioning of a GDEP enhancer element in operable fashion to a respective promoter may be achieved with no more than routine experimentation for an artisan.

The invention includes the use of vectors, preferably expression vectors, containing a nucleic acid including the GDEP enhancer sequence. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operably linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The expression vectors according to the invention comprise an enhancer element of the invention in a form suitable for directing tissue specific expression of an operably linked promoter/gene in a host cell. The expression vectors may include other promoters, additional enhancers, and other expression control elements (e.g., polyadenylation signals). Such regulatory sequences are described, for example, in Goeddel (1990) Methods Enzymol. 185:3-7. It is preferred that such regulatory sequences combine with the enhancer to direct expression of the gene only in certain host cells (i.e., in a tissue-specific manner). It will be appreciated by those skilled in the art that the design of the expression vector can depend on such factors as the choice of the host cell to be transformed, the level of expression of gene product desired, and the like. The expression vectors of the invention can be introduced into host cells to thereby produce proteins or peptides, including fusion proteins or peptides, or, alternatively, RNAs which may, e.g., act via anti-sense RNA silencing or RNA to affect gene expression.

In certain preferred embodiments, the invention is a mammalian expression vector containing the GDEP enhancer element. Examples of mammalian expression vectors suitable for use in the present invention include the pGL3-promoter vector, as described in the examples section (Promega, Madison, Wis.). When used in mammalian cells, the expression vector's control functions are provided by tissue specific regulatory elements. For example, heterologous promoters may be derived from polyoma, Adenovirus 2, cytomegalovirus and Simian Virus 40 (SV40) and, in the instant case, tissue specific expression is driven by the GDEP enhancer element. For other expression systems for eukaryotic cells, see chapters 16 and 17 of Sambrook, J. et al., Molecular Cloning: A Laboratory Manual, 2nd ed., Cold Spring Harbor Laboratory, Cold Spring Harbor Laboratory Press, Cold Spring Harbor, N.Y., 1989. A recombinant mammalian expression vector according to the invention is therefore capable of directing expression of a gene of interest preferentially in a particular cell type, namely, a neural retinal cell.

In certain embodiments, the invention provides a vector for treating retinal-related conditions by gene therapy. Such vectors include: (a) a therapeutic gene under control of a gene promoter; and (b) the human GDEP enhancer sequence set forth in SEQ ID NO:1 or a sequence with substantial sequence homology thereto. The sequence is operably linked to the gene promoter and confers retinal specific expression on the therapeutic gene. Such vectors preferably utilize a heterologous promoter and take the form of a virus vector such as, for example, an adeno-virus vector, an adeno-associated virus (AAV) vector, or a retrovirus.

In certain embodiments the gene to be expressed in retinal specific fashion is a reporter gene. Suitable reporter genes include, but are not limited to, reporter gene encoding luciferase, chloramphenicol acetyl transferase, beta-lactamase, green fluorescent protein, or beta-galactosidase. Such constructs are useful in assays, as subsequently described, and to visualize the temporal and/or spatial expression of GDEP enhancer-containing constructs.

In other embodiments, the gene to be expressed in a retinal specific manner is a gene encoding a native or heterologous gene product desirable for gene therapy. Such genes are referred to herein as "therapeutic genes." For example, For example, introduction of genes that encode antioxidants such as ECSOD (human extracellular superoxide dismutase) or CAT (catalase) have been used in mouse models to provide suppression of neuronal and axonal loss associated with diseases such as optic neuritis and multiple sclerosis. (Qi, X et al Invest Opthalmol Vis Sci December 2007 48(12):5360-70.) Another use for retinal gene therapy is the introduction of a native gene product to the retina where a deficient one currently resides. An example of this approach is in Leber congenital amaurosis which is caused by RPE65 gene mutations. Functioning RPE65 genes have been successfully introduced in dogs even as late as 1 year of age, with the functioning gene restoring vision. (Aquirre et al. PLOS MEd Jun. 4, 2007, (6):e230). As is generally known, gene therapy of the retina has been shown to promote survival in degenerative disorders and to prevent vascular degeneration in age related macular degeneration. Human trials for age related macular degeneration include the use of the pigment epithelium derived factor, PEDF, gene. (Campochiaro et al. Human gene therapy Feb. 17, 2006(2): 167-176) The conditions and diseases noted in this paragraph are illustrative of "retinal-related conditions" that may be treated by therapeutic methods according to the invention.

In another embodiment, the invention provides a host cell comprising an isolated nucleic acid as described and claimed herein. Certain host cells comprise a GDEP enhancer sequence and a gene operably linked to a promoter that is not normally subject to transcriptional regulation by the GDEP enhancer sequence. Preferred host cells for use according to the invention are mammalian cells, including, but not limited to, primary cultured neural retinal cells or immortalized neural retinal cell lines. Host cells may be in the context of cell culture or in an in vivo setting. Thus, via gene transfer with appropriate expression vectors comprising a gene under the control of an enhancer element of the invention, it is possible to convert certain host cells into transformed cells which produce increased quantities of a desired gene product, preferably a product from a therapeutic gene.

Accordingly, the invention provides methods for retinal specific expression of a gene. Such methods include steps of: (a) providing a host cell containing: (i) a gene promoter; (ii) a gene operably linked to the gene promoter; and (iii) an enhancer sequence as set forth in SEQ ID NO:1 or a sequence with substantial sequence homology thereto wherein the enhancer sequence is operably linked to the gene promoter and confers retinal specific responsiveness thereon; and (b) subjecting the host cell to conditions suitable for retinal specific expression of the gene. The respective gene to be expressed is preferably a heterologous gene, more preferably a therapeutic gene.

In certain embodiments, the invention further provides methods for treating a retinal-related condition by gene therapy. Such a method includes the step of administering to an individual in need of such gene therapy an inventive vector described herein. Certain methods provide for retinal specific expression of a therapeutic gene and include the step of administering to an individual in need of retinal specific expression of a therapeutic gene a vector according to the invention In another aspect of the invention, methods of screening for an agent that may alter the activity of an enhancer sequence for GDEP are provided. Such methods include steps of: (a) providing a nucleic acid comprising (i) a gene promoter; (ii) a reporter gene operably linked to the gene promoter; and (iii) an enhancer sequence for GDEP as set forth in SEQ ID NO:1 wherein the enhancer sequence is operably linked to the gene promoter to confer retinal specific responsiveness thereon; (b) subjecting the nucleic acid to conditions suitable for the enhancer sequence to enhance expression of the reporter gene in the presence of the test agent; and (c) evaluating the expression of the reporter gene compared to a control nucleic acid that is exposed to the same conditions but without the test agent wherein a higher or lower expression than that of the control nucleic acid indicates that the agent may alter GDEP enhancer sequence activity.

Test agents contemplated for screening in accordance with the invention assay methods include any chemical entity which can potentially affect the ability of the GDEP enhancer element to modulate transcription activity. Candidate/test compounds include, for example, 1) peptides such as soluble peptides, including Ig-tailed fusion peptides and members of random peptide libraries (see, e.g., Lam, K. S. et al. (1991) Nature 354:82-84; Houghten, R. et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, F(ab')₂ Fab expression library fragments, and epitope-binding fragments of antibodies); and 4) small organic and inorganic molecules (e.g., molecules obtained from combinatorial and natural product libraries). Small molecules are particularly attractive candidate/test compounds because such chemical entities typically provide ease of delivery (e.g., oral administration) and their potency, efficacy and selectivity can be enhanced or modulated via deliberate chemical modification. Accordingly, methods directed at the identification of agents capable of altering GDEP gene transcriptional activity represent certain embodiments of the invention.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

This example describes cell lines, plasmid vector construction, transfection methods, and expression assays utilized in subsequent examples.

Cell Lines

All cell lines were obtained from the American Type Culture Collection (ATCC). Media and media additives were purchased from Fisher Scientific (Pittsburgh Pa.) unless otherwise specified. Prostate cancer cell line LnCAP fgc was cultured in RPMI 1640 supplemented with 10% fetal bovine serum (FBS), 2 mM L-glutamine, 10 mM HEPES, and 1 mM sodium-pyruvate. Prostate cancer cell line DU145 was cultured in EMEM (Eagle's minimum essential medium) with 2 mM L-glutamine and Earle's BSS, supplemented with 10% FBS 0.1 mM non-essential amino acids and 1 mM sodium pyruvate. Retinoblastoma cell line Y79 was cultured in RPMI 1640 supplemented with 20% FBS, 10 mM HEPES, and 1 mM sodium pyruvate. Breast cancer cell line MCF7 was cultured in EMEM, supplemented with 10% FBS 0.1 mM non-essential amino acids and 1 mM sodium pyruvate and supplemented with 0.01 mg/ml insulin (Novo Nordisk, Princeton N.J.). Prostate cell lines RWPE 1 and RWPE 2 were cultured in Keratinocyte SFM amended with the manufacturers supplied epidermal growth factor and bovine pituitary extract (Invitrogen, Carlsbad Calif.). For the testosterone assays, Hyclone charcoal stripped FBS was used and 10 nM testosterone (Sigma, St. Louis Mo.) was added to the appropriate samples.

Construction of Plasmid Vectors

Promoter Constructs

A series of promoter deletion vectors was created starting approximately 2.4 Kb from the identified transcription initiation site and decreasing by approximately 0.5 Kb. The initial set of vectors was created to identify regions of promoter activity 5' of the GDEP gene. A second set of vectors was later created to achieve maximal promoter activity.

PCR fragments were cloned into the promoterless pCAT 3.0 basic vector (Promega, Madison Wis.) using directional cloning and the vector restriction sites Kpn 1 and Bgl II. The 2.4 Kb upstream of the GDEP gene was amplified with PCR using the Expand High Fidelity PCR System (Roche, Indianapolis, Ind.) and primer set PRO-R (BamH 1) and PRO-F (Kpn 1) (Table 1) for a 2373 bp fragment encompassing −2341 PCAN1 gene to +32 (nucleotides measured from the most 5' RLM RACE transcription start site (FIG. 1). The 1 Kb fragment of the GDEP gene was amplified as above using primer set PRO-R (BamH 1) and PRO 1 kb-F (Kpn 1) (Table 1) for a 900 base pair fragment encompassing −868 of the GDEP gene to +32 (FIG. 1).

Other pCAT expression vectors were made using directional cloning of the digested 2.4 Kb promoter fragment and restriction sites as follows: 2 Kb promoter, the PCR product was digested with RSA 1 and BamH 1 yielding a 1887 bp product from −1855 to +32 and cloned into the Sma 1 Bgl II sites of pCAT basic. 1.3 Kb promoter, the PCR product was digested with Xho 1 and BamH 1 yielding a 1276 bp from −1244 to +32 and cloned into the Xho 1 and Bgl II sites of pCAT basic. 0.5 Kb promoter, the PCR product was digested with Xba 1 and BamH 1 yielding a 496 bp product from −464 to +32 and cloned into the Nhe 1 and Bam H 1 sites of the PCAT basic vector.

Finally, 4 additional pCAT expression vectors were created between the 1 and 2 KB expression vectors to further define GDEP promoter expression. These vectors were created using the pCAT 3.0 basic vector digested as above with KPN1 and BglII and PCR products created using the Expand High Fidelity PCR system, with PRO-R as the reverse primer and primers PC1CATF1 for a 1748 bp fragment, PC1CATF2 for a 1598 bp fragment, PC1CATF3 for a 1447 base pair fragment and PCATF4 for a 1148 bp fragment (Table 1).

TABLE 1

Primers used to create expression vectors.

| (a) PRIMER | (b) SEQUENCE | (e) SEQ ID NO: 1 |
|---|---|---|
| Promoter Primers | | |
| PRO-R (BamH 1) | CGGGATCCTCTTCTGCCTCCCTCTCTCA | 2 |
| PRO-F (Kpn 1) | GGGGTACCTTTTCAAGGTGCTCAGTTTTCA | 3 |

TABLE 1-continued

Primers used to create expression vectors.

| (a) PRIMER | (b) SEQUENCE | (e) SEQ ID NO: 1 |
|---|---|---|
| PRO 1kb-F (Kpn 1) | GGGGTACCCATTTTAAGGGAAAGAATGAGC | 4 |
| PC1CATF1 (Kpn 1) | GGGGTACCAGTTATGTCCAATGATA | 5 |
| PC1CATF2 (Kpn 1) | GGGGTACCACTACCCGATCTCCAACC | 6 |
| PC1CATF3 (Kpn 1) | GGGGTACCTAATACCATTCCGGCAGT | 7 |
| PC1CATF4 Kpn 1) | GGGGTACCAAGGAGGCTTAACACAGC | 8 |
| Intron Primers | | |
| Pcan1 Intron 3631 F | ACGCGTCGACGCTTCCTGCTGTGGCTAATC | 9 |
| Pcan1 Intron 6458 R | ACGCGTCGACCAAAGGCCGTACTGATGTT | 10 |
| Pcan1 Intron 6068 F | ACGCGTCGACAGCTAGTAGAGAGTCTATTGGACA | 11 |
| Pcan1 Intron 8175 R | ACGCGTCGACTCATGTAATCAATAACCATCTGTT | 12 |
| Pcan1 Intron 23992 F | ACGCGTCGACCAAACAACTGTGTGAAGTGAATTC | 13 |
| Pcan1 Intron 26187 R | ACGCGTCGACAAGTATGTGCTAATAAACAAAGAT | 14 |
| Pcan1 Intron 3 A F | ACGCGTCGACGCTTCCTGCTGTGGCTAATC | 15 |
| Pcan1 Intron 3 D R | ACGCGTCGACACCAATCTTTCTGGTCCATC | 16 |
| Pcan1 Intron 3 E F | (c) ACGCGTCGACGATAAAACTGTAAACTGTGAGCAGAA | 17 |
| Pcan1 Intron 3 H R | ACGCGTCGACAGGGCTTGCCTGAATAGAC | 18 |
| Pcan1 Intron 3 I F | ACGCGTCGACTCCTGAGACAATTGTGCATAAAA | 19 |
| Pcan1 Intron 3 I R | (d) ACGCGTCGACTGTACACCTGCTTCAAGTCTTTTC | 20 |
| Pcan1 Intron 3 J F | ACGCGTCGACCAAGTGGTTAAATGTCCAAAA | 21 |
| Pcan1 Intron 3 J R | ACGCGTCGACCATCAACAAGGGACCCATTCA | 22 |
| Pcan1 Intron 13 A F | ACGCGTCGACCAAACAACTGTGTGAAGTAGATTCTG | 23 |
| Pcan1 Intron 13 D R | ACGCGTCGACTCAAAAGGGAAGAGGCTTCA | 24 |
| Pcan1 Intron 13 E F | ACGCGTCGACAGGCCCTGAGCACAATTACA | 25 |
| Pcan1 Intron 13 F R | ACGCGTCGACAGCTGGGGTTTAACTGAGCA | 26 |
| Pcan1 Intron 13 G F | ACGCGTCGACTGGAAAGAAATTCCCAGCAC | 27 |
| Pcan1 Intron 13 H R | ACGCGTCGACTTTTTCCCCTGGGCTAAGAT | 28 |

Letters in Bold are nucleotides added to the genomic sequence to form a restriction site.

Enhancer Constructs

Luciferase vectors were constructed using the pGL3 vector (Promega, Madison Wis.). All fragments were cloned into the pGL3-promoter vector 3' of the luciferase gene in the Sal 1 restriction site. The 40 KB GDEP intron was divided into 17 PCR fragments of approximately 2.5 KB (FIG. 1). Further subcloning of the intron fragments occurred with those fragments that exhibited enhancer activity. Intron fragment 3 was further subdivided into smaller fragments of approximately 1 KB. Amplified primers were PCAN1 Intron 3A F and 3D R (1058 bp fragment), PCAN1 Intron 3E F and 3H R (1157 bp fragment), PCAN1 Intron 3I F and 3J R (589 bp fragment). Intron fragment 13 was subdivided similarly using the following primer sets PCAN1 Intron 13A F-13D R (1116 bp fragment), and PCAN1 Intron 13E F-13H R (1079 bp fragment). All intron fragments were cloned into the pGL3-promoter vector Sal 1 site. GDEP In 3 I-J and GDEP In13 E-H fragments were further subdivided into smaller deletion fragments using the primers PCAN1 Intron 3I F and 3I R (353 bp fragment), PCAN 1 Intron 3J F and 3J R (309 bp fragment), PCAN1 Intron 13E F and 13F R (619 bp fragment) and PCAN 1 Intron 13G F and 13H R (439 bp fragment) and these fragments were cloned into pGL3-promoter. PCR primers used for cloning fragments with activity are listed in Table 1.

The entirety of the nucleotide sequence defined by primer pair 13E F (SEQ ID NO:25) and 13F R (SEQ ID NO:26) is set forth below as SEQ ID NO:1:

```
aggccctgagcacaattacaaaccaaaccagattcatccactgaagcctc
ttcccttttgacgttttcaatcatcatcttttccttttctattagatttt
gaatatccttaagtggcactcatctgatgttaaagtgtcacgccttgtgc
catgcctcagcctgatgttcctcatgacagtgttctaaatcttatcccaa
ccaaaattcacttgtgcattgcccttcctccttgttctatcatcacaaa
atctgtggtatttaattggtatgtagtttcaataagaactgatgagctga
ctaggttcaaatgttgggaaggccatctagaaattatcgattatgccaaa
aagcaaagctaagagagagacttccaagccatacttgatactggagaaga
ctgtatttgcaactatttcaagtttctgctattccttggccatcaatgcc
ttcttcacattgtggttatgtcattatatattttcactcctgtaggagaa
gacttaaaacatttttttaaaattcttaagttattgtctctttattgcac
tgcaattttgtctgttgcttagaatttgtgatggaaagaaattcccagca
ccttgtaatccaggtcttagcctttccagtctatccagattgctcagtta
aaccccagct
```

Plasmid DNA Transfections

DNA was purified using Qiagen Plasmid Kits (Qiagen, Valencia, Calif.). Cells were transiently transfected using lipofectamine 2000 (Invitrogen, Carlsbad, Calif.) according to the manufacturer's directions. For Luciferase assays the 24 well plate protocol was used. Briefly, $0.5 \times 10^5$ cells were co transfected using 2 uL of Lipofectamine 2000 and 0.3 μg of PCMV/Sport β-galactosidase vector (Invitrogen, Carlsbad, Calif.) as a control and 1 μg of plasmid construct. For CAT assays 12 well plates were used and quantities of all components were doubled.

Chloramphenicol Acetyltransferase (CAT) Expression Assays

CAT activity was measured using the CAT Enzyme Assay System with Reporter Lysis Buffer (Promega, Madison Wis.). Transfections were incubated for 48 hours and lysed using 250 uL of 1× Reporter Lysis buffer per individual transfection. CAT activity in the lysate was measured according to the protocol with 125 ul of lysate and 20 hour incubation. Counts per minute (cpm) were measured using liquid scintillation counting. CAT activity was normalized for transfection efficiency by dividing by the β-galactosidase activity measured using the protocol from Molecular Cloning $3^{rd}$ ed. (9).

Luciferase Expression Assays

Luciferase activity was measured using the Luciferase Assay System with Reporter Lysis Buffer (Promega, Madison Wis.). Transfections were incubated between 24 and 48 hours, and lysed using 100 uL of 1× Reporter Lysis buffer per transfection. Luciferase activity in 10 uL of lysate was measured using a Td 20/20 luminometer (Turner Biodesigns, Sunnyvale, Calif.) and a 10 second read time. Luciferase activity was normalized for transfection efficiency using β-galactosidase activity as outlined above.

Example 2

Promoter Determination

Prostate

Figure 2:
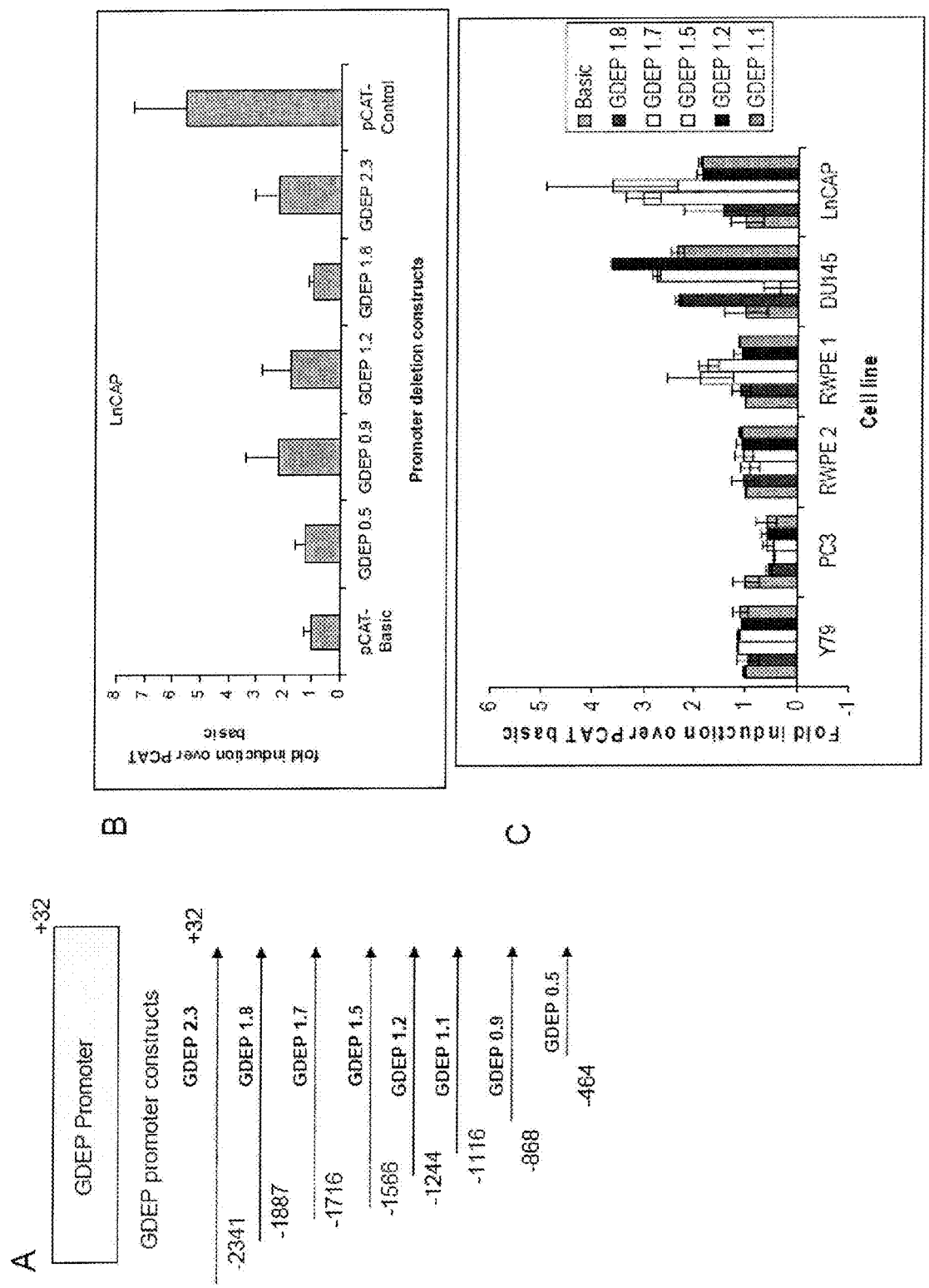
FIG. 2 depicts GDEP promoter expression in prostate cell lines. A) GDEP promoter deletion constructs used for expression studies. B) Transient transfection CAT assay of the 5 initial deletion vectors. Response is measured as fold induction over the promoterless pCAT basic vector. C) Transient transfection assays of additional deletion vectors in multiple prostate cell lines. Response is measured as fold induction over the promoterless pCAT basic vector. Results are the compilation of at least 2 independent transfections.

To determine the regulatory sequence driving tissue specific expression of GDEP the inventors first investigated the 2.4 Kb putative promoter region immediately upstream of the transcription start site. A series of deletion vectors was made using chloramphenicol acetyltransferase to determine the minimal length of genomic sequence needed to provide the maximal reporter construct expression. For prostate cancer cell line LnCAP the 0.9 and 2.3 KB constructs exhibited promoter activity, exhibiting 2 fold greater activity over the basic vector (FIG. 2).

Finer deletion constructs were made between the 0.9 and 2 KB constructs. These promoters were transfected into a number of prostate cell lines including LnCAP, RWPE 1, and RWPE 2 which express GDEP as well as PC3 and DU145 which have no detectable level of GDEP expression. The 1.5 Kb vector exhibited the highest level of expression in LnCAP cells with 3.6 times greater expression than that of the basic vector. Similar levels of expression in DU145 (2.75 fold) and slightly less expression in RWPE1 was found when tested in other prostate cell lines. Other constructs that exhibited high levels of expression in a single cell line include the 1.2 KB construct with the highest expression in DU145, 3.6 times greater expression than the basic vector. The 1.7 KB vector which exhibited expression 3 times greater than the basic vector in the LnCAP cell line and 1.9 times greater activity in RWPE 1 cells (FIG. 2). This demonstrates that the GDEP promoter fragment has activity in a wide range of prostate cells, and the variation in promoter expression between cell lines.

Retina

Figure 3:
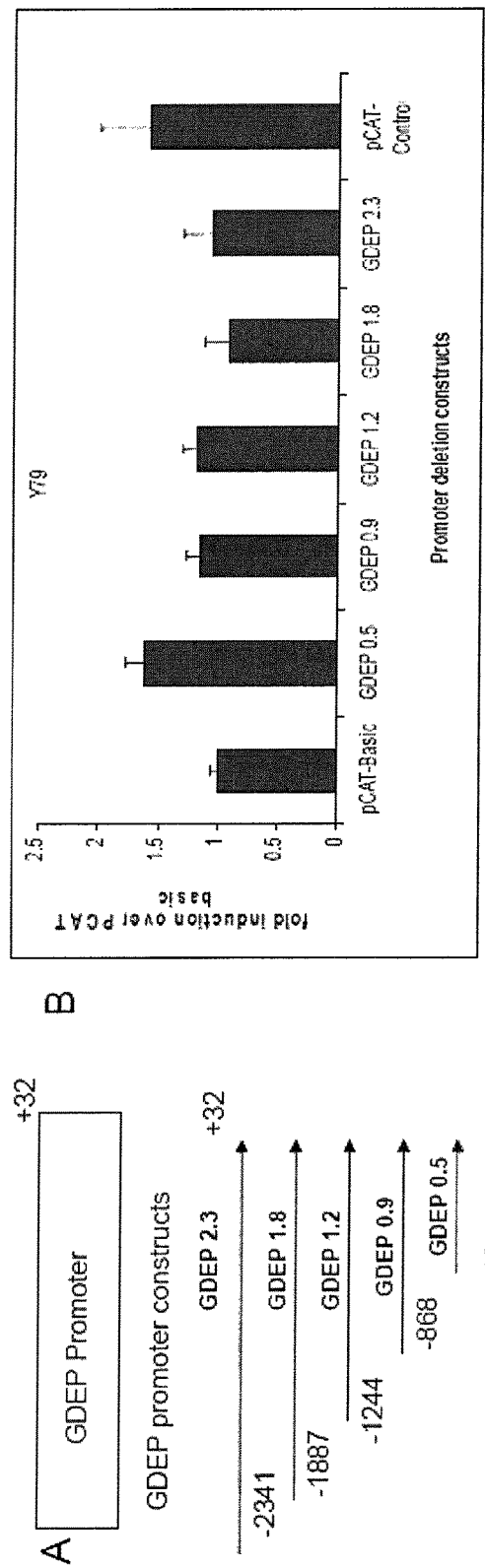
FIG. 3 depicts GDEP promoter expression in Y79 retinoblastoma cell line. A) GDEP promoter deletion constructs used for expression studies. B) Transient transfection CAT assay of the 5 initial deletion vectors. Response is measured as fold induction over the promoterless pCAT basic vector. Results are the compilation of at least 2 independent transfections.

Because GDEP is also expressed in retinal cells the inventors investigated the expression of the promoter deletion constructs in retinoblastoma cell line Y79. The only construct that showed any expression above the basic vector was the 0.5 KB vector which exhibited 1.5 times the activity of the basic vector. This activity though weak, was equivalent or greater than that of the positive control vector (FIG. 3).

Example 3

Enhancer Determination

Prostate

Figure 4:
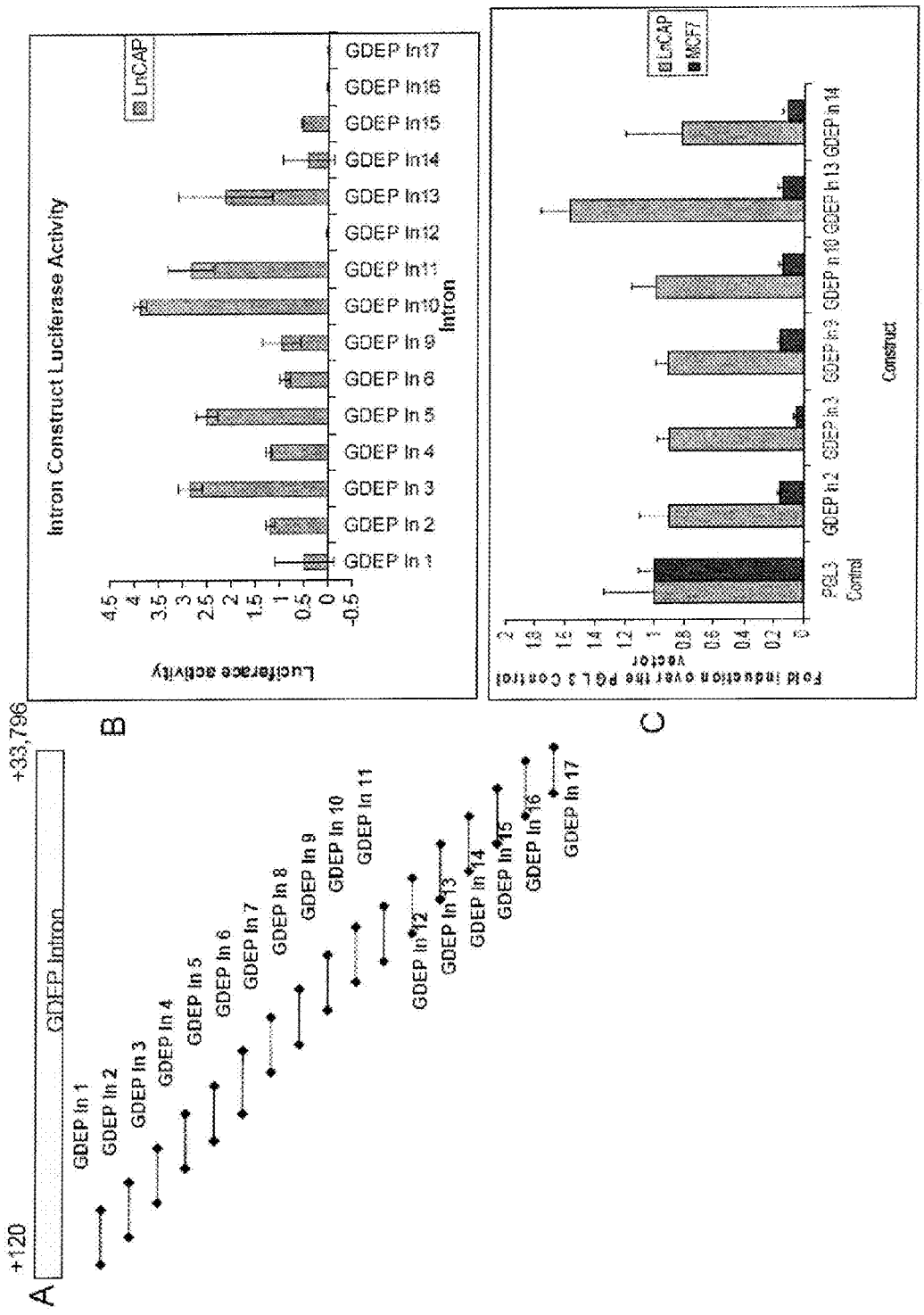
FIG. 4 illustrates relative luciferase activity of the intron fragment enhancer expression constructs in prostate cancer cell line LnCAP and breast cancer cell line MCF7. A) Schematic of the position of each enhancer constructs with respect to the GDEP gene. B) Luciferase expression of each enhancer construct, normalized to average luciferase expression activity. C) Transient transfection assay of luciferase activity of selected intron constructs in LnCAP prostate cancer cell line and MCF7 breast cancer cell line normalized to the pGL3-control vector. Results are the compilation of at least 2 independent transfections.

Because the upstream portion of GDEP exhibited consistent but low levels of reporter gene expression, potential regulatory elements in the 40 KB intron of the GDEP gene were investigated by the inventors. 3 KB portions of the 40 KB intron were cloned into the Sal 1 restriction site of the pGL3-promoter vector. This site is 3' of the luciferase gene. Constructs were then tested for luciferase activity by transfecting into LnCAP cells. Relative luciferase activity of 15 of the constructs with respect to one another is shown in (FIG. 4). Intron fragments 3, 5, 10, 11, and 13 exhibited the highest activity. Intron fragments 3, 10 and 13 were chosen for further analysis because they were spaced throughout the intron and likely represented entirely separate regulatory elements.

To determine if the intron constructs exhibited activity comparable to a control plasmid containing the SV 40 enhancer region (pGL3-control) intron fragment constructs 2, 3, 9, 10, and 13, and 14 were transfected into LnCAP. Breast cancer cell line MCF7 served as a negative control cell line because GDEP is not expressed in breast tissue or the MCF7 breast cancer cell line. In prostate cell line LnCAP luciferase activity was equal to or greater than that of pGL3-control while this activity was not exhibited in the MCF 7 cell line (FIG. 4).

Figure 5:
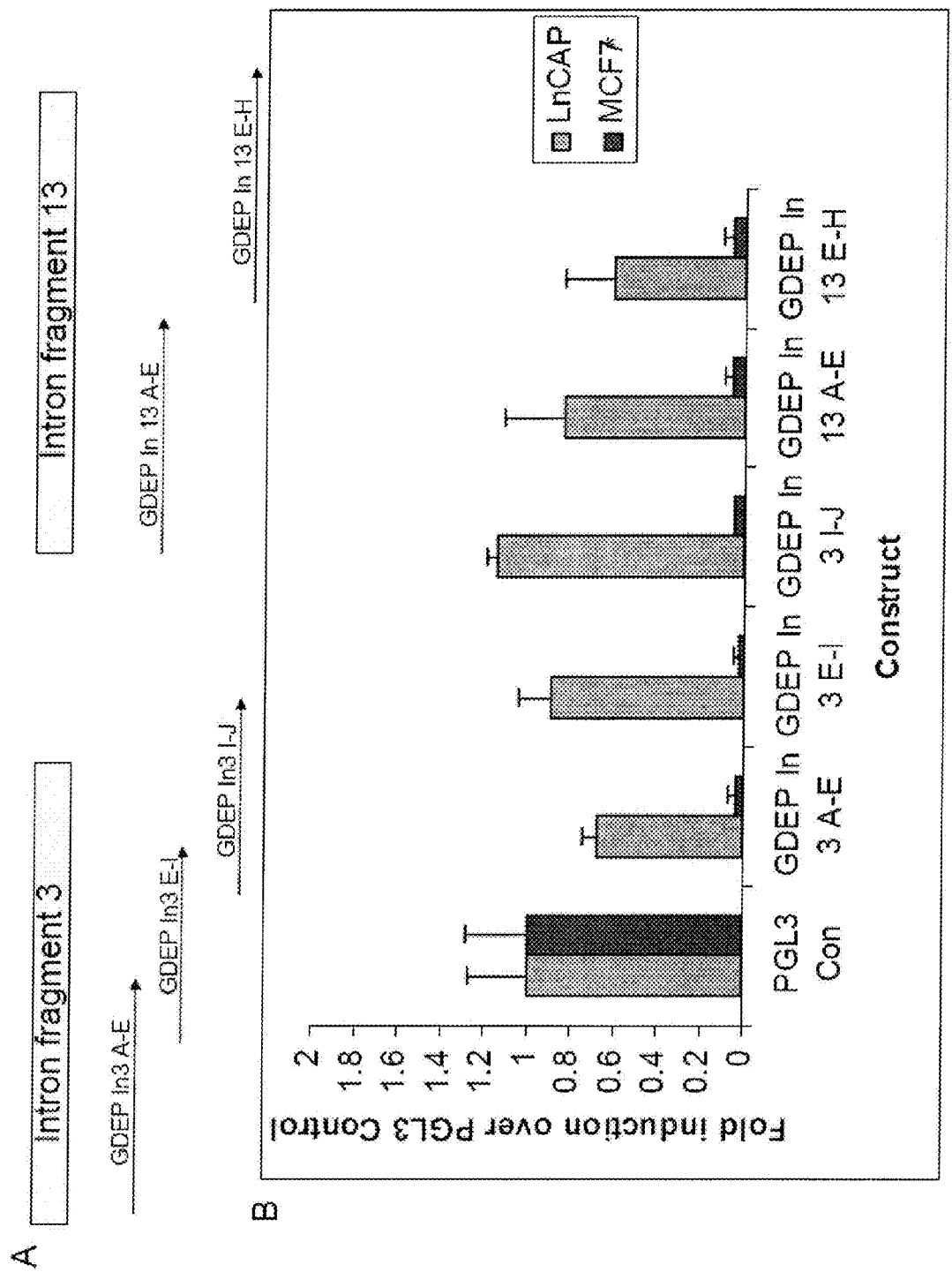
FIG. 5 illustrates relative luciferase activity of the deletion intron fragment enhancer expression constructs in prostate cancer cell line LnCAP and breast cancer cell line MCF7. A) Schematic of the position of each deletion enhancer construct with respect to the original intron constructs. B). Transient transfection assay of luciferase activity of selected intron constructs in LnCAP prostate cancer cell line and MCF7 breast cancer cell line normalized to the pGL3-control vector. Results are the compilation of at least 3 independent transfections.

Two of the constructs with the highest activity, intron fragment 3 and 13 were chosen for further deletion analysis. These constructs were divided into approximately 1 Kb fragments and inserted into the pGL3-promoter vector and transfected into LnCAP and MCF7 cell lines (FIG. 5). All of the fragments exhibited approximately the same level of expression as the pGL3-control vector. GDEP In 3 I-J exhibited expression slightly higher than that of the control vector in LnCAP cells and was selected for further study.

Figure 6:
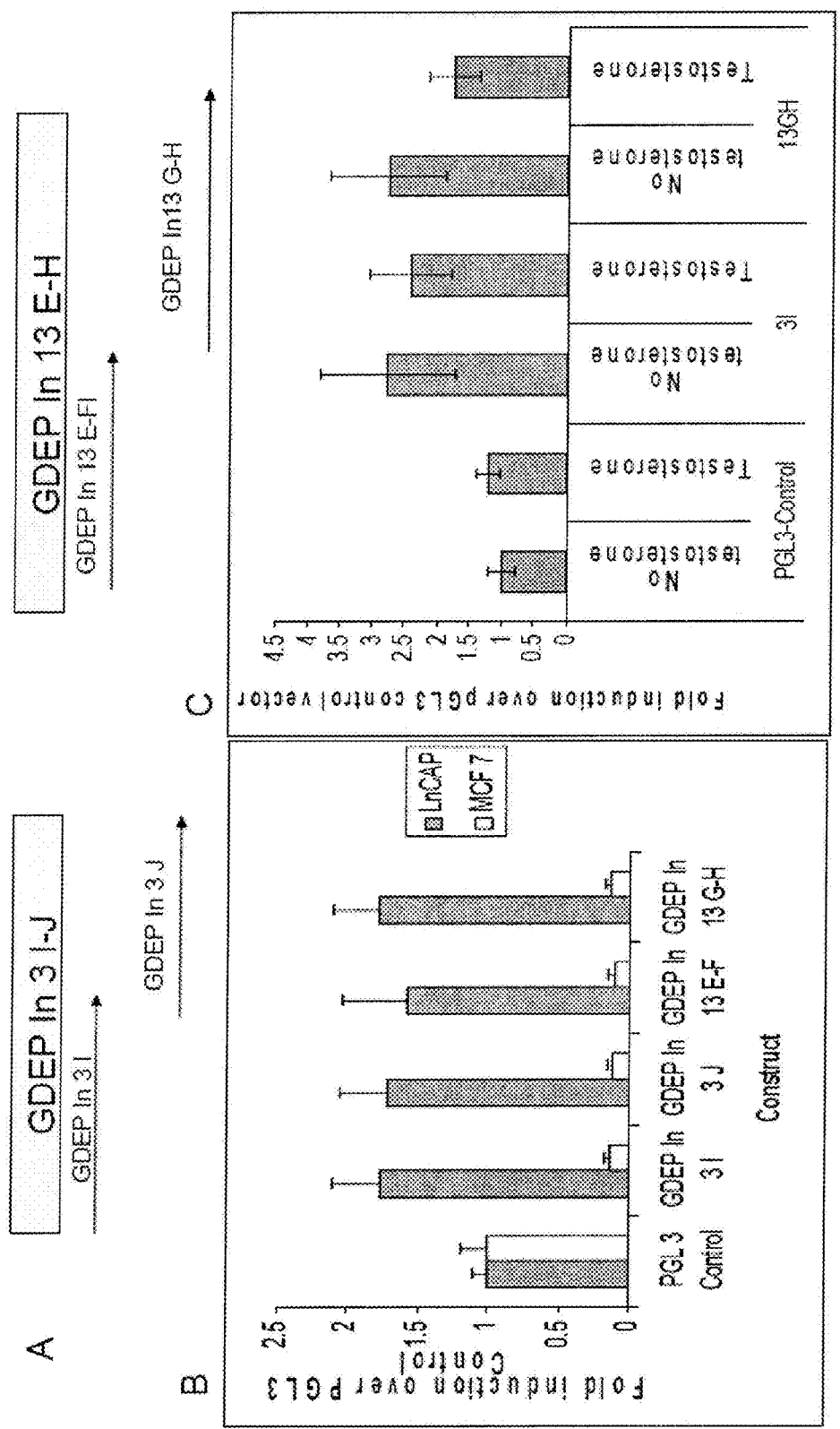
FIG. 6 illustrates relative luciferase activity of the smallest intron fragment enhancer expression constructs in prostate cancer cell line LnCAP and breast cancer cell line MCF7. A) Schematic of the position of each small enhancer construct with respect to the larger intron constructs. B). Transient transfection assay of luciferase activity of small intron constructs in LnCAP prostate cancer cell line and MCF7 breast cancer cell line normalized to the pGL3-control vector. Results are the compilation of 9 independent transfections. C) Transient transfection of luciferase activity of small intron constructs in LnCAP prostate cancer cell line in the presence and absence of testosterone normalized to the pGL3-control vector. Results are the compilation of at least 3 independent transfections.

Two fragments were selected for further analysis; the fragment exhibiting the highest activity (GDEP In 3 I-J) for prostate cell line LnCAP and GDEP In13 E-H which exhibited a lower level of prostate expression. These constructs were divided into 300 to 600 base pair fragments. For LnCAP constructs, GDEP In 3I and GDEP In 13 G-H exhibited expression almost double that of the pGL3-control vector (1.8 fold induction) (FIG. 6).

Enhancer activity for the fragments was tested for induction in the presence and absence of 10 nM testosterone to determine if the enhancer activity was sensitive to androgen. None of the enhancer constructs showed a significant response to androgen, enhancer activity may be slightly decreased in response to androgen but this was not significant (FIG. 6).

Retina

Figure 7:
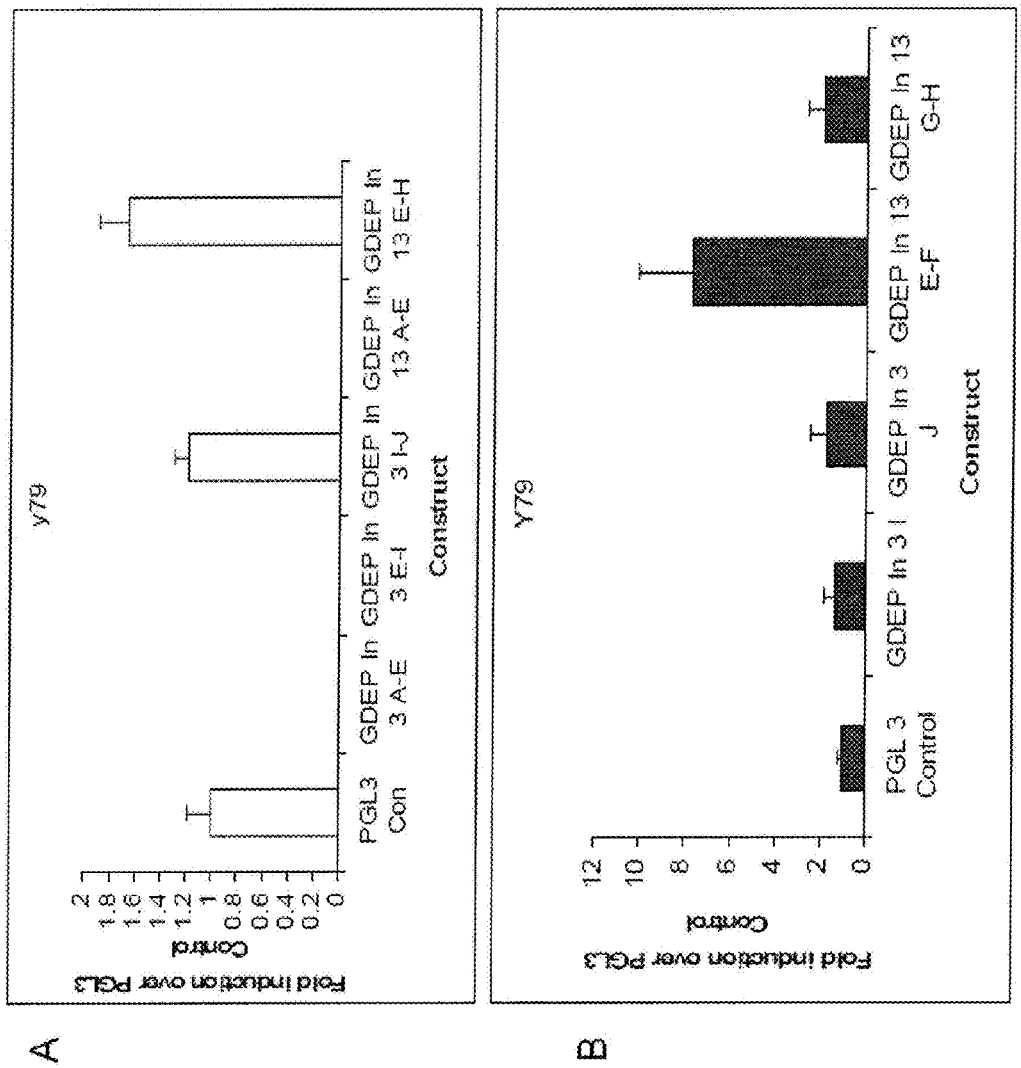
FIG. 7 illustrates relative luciferase activity of the deletion intron fragment enhancer expression constructs and the smallest enhancer expression constructs in retinoblastoma cancer cell line. A) Transient transfection assay of luciferase activity of selected intron constructs in Y79 retinoblastoma cell line normalized to the pGL3-control vector. Results are the compilation of at least 3 independent transfections. B) Transient transfection assay of luciferase activity of small intron constructs in retinoblastoma cell line normalized to the pGL3-control vector. Results are the compilation of 9 independent transfections.

To determine if the same constructs that increased expression in prostate could also increase expression in retinal cells the inventors transfected Y79 with 2 constructs GDEP In 3 I-J which showed the most expression in LnCAP cells and GDEP In 13 E-H which exhibited the least expression in LnCAP cells. Y79 cells responded to GDEP 3I-J in a similar fashion to that of LnCAP. Expression of luciferase was slightly increased over that of the control vector. Reporter construct GDEP In 13 E-H exhibited a greater expression level in Y79 retinoblastoma cells than that of prostate with reporter expression 1.8 fold higher than that of the control vector (FIG. 7). The smaller intron deletion vectors were also transfected into the Y79 cell line and activity was determined. The greatest enhancer activity was seen in retinoblastoma cell Y79 for construct GDEP In 13 E-F which exhibited an 8 fold increase in expression over the control vector (FIG. 7).

Those skilled in the art will recognize, or be able to ascertain using no more then routine experimentation, numerous equivalents to the specific polypeptides, nucleic acids, methods, assays and reagents described herein. Such equivalents are considered to be within the scope of this invention and encompassed by the following claims.

REFERENCES

1. Lumniczky K, Safrany G. Cancer gene therapy: combination with radiation therapy and the role of bystander cell killing in the anti-tumor effect. Pathol Oncol Res. 2006; 12:118-24.
2. Robson T, Hirst D G. Transcriptional Targeting in Cancer Gene Therapy. J Biomed Biotechnol. 2003; 2003:110-137.
3. Palmer D H, Young L S, Mautner V. Cancer gene-therapy: clinical trials. Trends Biotechnol. 2006; 24:76-82.
4. Olsson P, et al. GDEP, a new gene differentially expressed in normal prostate and prostate cancer. Prostate. 2001; 48(4):231-41.
5. Reding D J, et al. Identification of a gene frequently mutated in prostate tumors. Med Oncol. 2001; 18:179-87.
6. Cross D, et al. Expression and initial promoter characterization of PCAN1 in retinal tissue and prostate cell lines. Med Oncol. 2004; 21:145-53.
7. Stanizzi M A, Hall S J. Clinical experience with gene therapy for the treatment of prostate cancer. Rev Urol. 2007; 9 Suppl 1:S20-8.
8. Sieving P A, Collins F S. Genetic ophthalmology and the era of clinical care. JAMA. 2007; 297:733-6.
9. Sambrook J, Russell D. Molecular Cloning: A Laboratory Manual. Cold Spring Harbor Laboratory, Cold Spring Harbor, N.Y., 2001, pp 17.48-17.51.
10. Verhaegh G W, van Bokhoven A, Smit F, Schalken J A, Bussemakers M J. Isolation and characterization of the promoter of the human prostate cancer-specific DD3 gene. J Biol Chem. 2000; 275:37496-503.
11. Latham J P, Searle P F, Mautner V, James N D. Prostate-specific antigen promoter/enhancer driven gene therapy for prostate cancer: construction and testing of a tissue-specific adenovirus vector. Cancer Res. 2000; 60:334-41.
12. Tsui K H, Wu L, Chang P L, Hsieh M L, Juang H H. Identifying the combination of the transcriptional regulatory sequences on prostate specific antigen and human glandular kallikrein genes. J Urol. 2004; 172:2029-34.
13. Noss K R, Wolfe S A, Grimes S R. Upregulation of prostate specific membrane antigen/folate hydrolase transcription by an enhancer. Gene. 2002; 285:247-56.
14. Good D, et al. Cloning and characterization of the prostate-specific membrane antigen promoter. J Cell Biochem. 1999; 74:395-405.
15. van der Poel H G, et al. A novel method for the determination of basal gene expression of tissue-specific promoters: an analysis of prostate-specific promoters. Cancer Gene Ther. 2001; 8:927-35.
16. Li H W, Li J, Helm G A, Pan D. Highly specific expression of luciferase gene in lungs of naive nude mice directed by prostate-specific antigen promoter. Biochem Biophys Res Commun. 2005; 334:1287-91.
17. Riegman P H, Vlietstra R J, van der Korput J A, Brinkmann A O, Trapman J. The promoter of the prostate-specific antigen gene contains a functional androgen responsive element. Mol Endocrinol. 1991; 5:1921-30.
18. Weng J, Ma W, Mitchell D, Zhang J, Liu M. Regulation of human prostate-specific G-protein coupled receptor, PSGR, by two distinct promoters and growth factors. J Cell Biochem. 2005; 96:1034-48.
19. Schuur E R, et al. Prostate-specific antigen expression is regulated by an upstream enhancer. J Biol Chem. 1996; 271:7043-51.
20. Cleutjens K B, et al. An androgen response element in a far upstream enhancer region is essential for high, androgen-regulated activity of the prostate-specific antigen promoter. Mol Endocrinol. 1997; 11:148-61.
21. Watt F, et al. A tissue-specific enhancer of the prostate-specific membrane antigen gene, FOLH1. Genomics. 2001; 73:243-54.
22. Cheng W S, et al. A novel TARP-promoter-based adenovirus against hormone-dependent and hormone-refractory prostate cancer. Mol Ther. 2004; 10:355-64.
23. Lee S J, et al. Novel prostate-specific promoter derived from PSA and PSMA enhancers. Mol Ther. 2002; 6:415-21.
24. Cheng W S, Dzojic H, Nilsson B, Totterman T H, Essand M. An oncolytic conditionally replicating adenovirus for hormone-dependent and hormone-independent prostate cancer. Cancer Gene Ther. 2006; 13:13-20.
25. Fong S L, Fong W B. Elements regulating the transcription of human interstitial retinoid-binding protein (IRBP) gene in cultured retinoblastoma cells. Curr Eye Res. 1999; 18:283-91.

26. Borst D E, et al. Structural characterization and comparison of promoter activity of mouse and bovine interphotoreceptor retinoid-binding protein (IRBP) gene 5' flanking regions in WERI, Y79, chick retina cells, and transgenic mice. Curr Eye Res. 2001; 23:20-32.
27. Pappu K S, et al. Dual regulation and redundant function of two eye-specific enhancers of the Drosophila retinal determination gene dachshund. Development. 2005; 132: 2895-905.
28. Poulin F, et al. In vivo characterization of a vertebrate ultraconserved enhancer. Genomics. 2005; 85:774-81.
29. Nie Z, Chen S, Kumar R, Zack D J. RER, an evolutionarily conserved sequence upstream of the rhodopsin gene, has enhancer activity. J Biol Chem. 1996; 271:2667-75.
30. Plaza S, Dozier C, Langlois M C, Saule S. Identification and characterization of a neuroretina-specific enhancer element in the quail Pax-6 (Pax-QNR) gene. Mol Cell Biol. 1995; 15:892-903.

What is claimed is:

1. An isolated nucleic acid comprising:
   (a) a human Gene Differentially Expressed in Prostate (GDEP) enhancer sequence consisting of SEQ ID NO: 1, and
   (b) a heterologous eukaryotic gene promoter that is operably linked to said enhancer sequence, wherein said enhancer sequence confers retinal specific responsiveness on the operably linked heterologous gene promoter.

2. The isolated nucleic acid according to claim 1 wherein the nucleic acid is an expression vector.

3. An isolated host cell comprising an isolated nucleic acid, the isolated nucleic acid comprising:
   (a) a human GDEP enhancer sequence consisting of SEQ ID NO: 1, and
   (b) a heterologous eukaryotic gene promoter that is operably linked to said enhancer sequence, wherein said enhancer sequence confers retinal specific responsiveness on the operably linked heterologous gene promoter;
   wherein said host cell is a primary cultured neural retinal cell.

4. An isolated host cell comprising an isolated nucleic acid, the isolated nucleic acid comprising:
   (a) a human GDEP enhancer sequence consisting of SEQ ID NO: 1, and
   (b) a heterologous eukaryotic gene promoter that is operably linked to said enhancer sequence, wherein said enhancer sequence confers retinal specific responsiveness on the operably linked heterologous gene promoter;
   wherein said host cell is a cell of an immortalized neural retinal cell line.

5. A method for retinal specific expression of a gene, comprising: (a) providing a host cell containing a nucleic acid comprising (i) a GDEP enhancer sequence consisting of SEQ ID NO: 1, said enhancer sequence operably linked to a heterologous eukaryotic gene promoter to confer retinal specific responsiveness thereon; and (ii) a gene operably linked to said heterologous gene promoter; and (b) subjecting the host cell to conditions suitable for retinal specific expression of said gene, wherein the host cell is a primary cultured neural retinal cell or a cell of an immortalized neural retinal cell line.

6. An in vitro method for screening for an agent that modulates the activity of a GDEP enhancer sequence, comprising:

(a) providing a nucleic acid comprising (i) the GDEP enhancer sequence consisting of SEQ ID NO: 1, said enhancer sequence operably linked to a heterologous eukaryotic gene promoter to confer retinal specific responsiveness thereon; and (ii) a reporter gene operably linked to said heterologous gene promoter;

(b) subjecting the nucleic acid to conditions suitable for the enhancer sequence to enhance expression of the reporter gene in the presence of a test agent;

(c) assaying the reporter by measuring the expression level or activity of the reporter;

(d) comparing the expression level of the reporter gene in the presence of the test agent to the expression level of the reporter gene in the absence of said agent; and wherein a higher or lower expression of the reporter gene indicates that the agent may modulate GDEP enhancer sequence activity.

7. A vector for treating retinal-related conditions by gene therapy, comprising:

(a) a therapeutic gene under control of a heterologous eukaryotic gene promoter; and (b) a human GDEP enhancer sequence consisting of SEQ ID NO: 1, wherein said enhancer sequence is operably linked to the heterologous eukaryotic gene promoter and confers retinal specific expression on the therapeutic gene.

8. The vector of claim 7, wherein said vector is a virus vector.

9. The vector of claim 7, wherein said vector is an adenovirus vector.

10. The vector of claim 7, wherein said vector is an adeno-associated virus (AAV) vector.

11. The vector of claim 7, wherein said vector is a retrovirus vector.

* * * * *